Aug. 20, 1974 A. BARBERET Plant Pat. 3,593
CARNATION PLANT
Filed Nov. 10, 1972
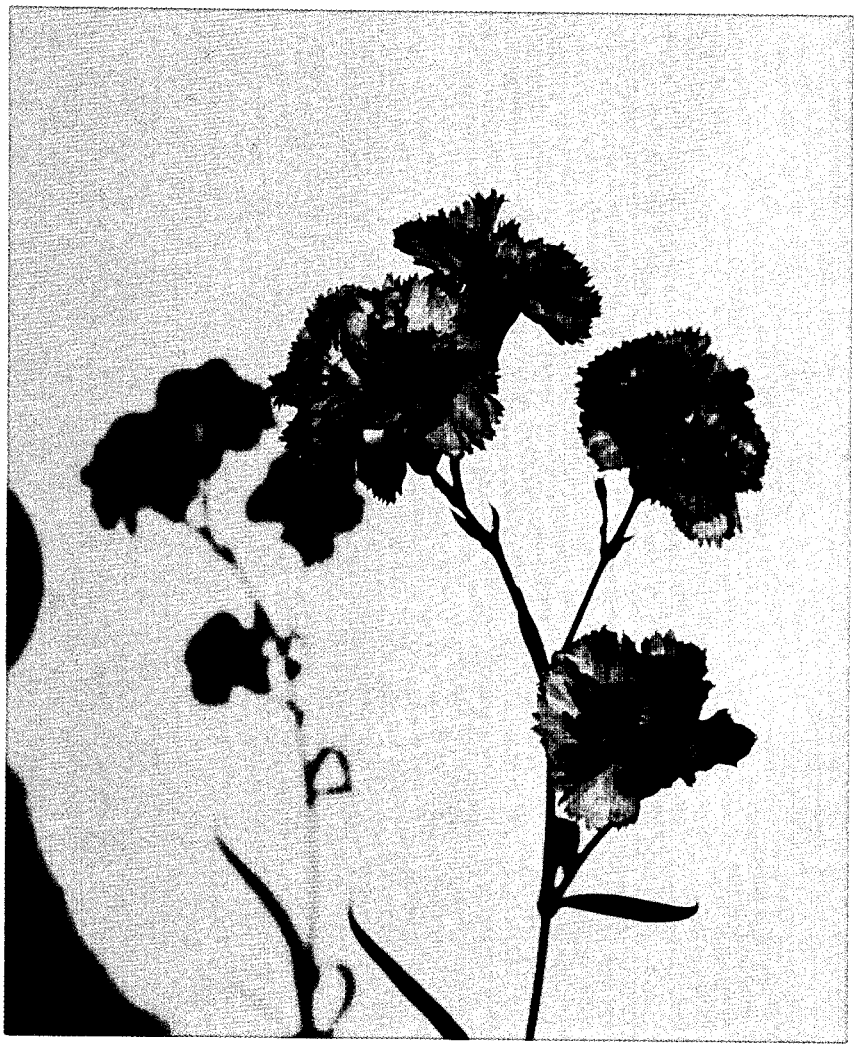

United States Patent Office

Plant Pat. 3,593

Patented Aug. 20, 1974

3,593

CARNATION PLANT

Alexandre Barberet, La Londe, France, assignor to Laboratoire de Physiologie Vegetale de La Londe, La Londe, France Filed Nov. 10, 1972, Ser. No. 305,606
Int. Cl. A01h 5/00
U.S. Cl. Plt.—73 1 Claim

ABSTRACT OF THE DISCLOSURE

A new variety of carnation plant originated as a hybrid seedling resulting from a cross of two varieties of carnation plants in the personal collection of the applicant and distinguished by a very vigorous growth habit, strong stems, uniform coloring and superior productivity.

Background of the New Plant

My new variety of carnation plant is the result of breeding efforts carried on by me at La Londe, France, since 1969, with the object of producing improved varieties of carnation plants and in the instant case, to produce a spray variety of miniature carnation having improved productivity over varieties such as Royalette (unpatented). This particular seedling was selected for propagation and test because it appeared to exhibit desirable characteristics of growth and blossom color and asexual propagation of this plant under my direction and by means of cuttings through many generations at La Londe, France, has demonstrated that its distinctive physiological features are firmly fixed and hold true from generation to generation.

Description of the Drawings

This new variety of carnation plant is illustrated by the accompanying photographic drawings which show the form and growth characteristics of the new plant and the development and final form of the blossoms.

Description of the New Plant

The following is a detailed description of this new carnation variety with the color designations according to The RHS Colour Chart published by The Royal Horticultural Society at London, England.

THE PLANT

Origin: Seedling.
Parentage:
*Seed Parent.*—Carnation 7V2 (unnamed, unpatented).
*Pollen Parent.*—Carnation 191V (unnamed, unpatented).
Classification:
*Botanic.*—Hybrid-Perpetual Flowering Carnation.
*Commercial.*—Spray variety—Miniature.
Form: Normally branched and leafy.
Height: About 45 cm.
Growth: Vigorous and erect with normal upright branching.
Foliage: Quantity—Medium.
*Leaf Shape.*—Lanceolate and up to 14.7 cm. long.
*Texture.*—Smooth.
*Color.*—Upper side—Greyed-Green Group 189B. Under Side—Greyed-Green Group 189B.
*Ribs.*—One axial rib well visible on the under side of the leaf.
*Petioles.*—None. Leaf is amplexicaul.

THE BUD

Form: Ovoid to cylindrical.
Size: Medium. Diameter: Up to 1.3 cm. Depth: Up to 2.7 cm.

Opening: Bud opens slowly.
Color: Green when sepals first divide and when petals begin to unfurl.
Sepals: Sepals stand up.
*Color.*—Inside—Light Green. Outside—Green.
Calyx: Large, long and funnel-like in shape.
*Aspect.*—Smooth.

THE FLOWER

Blooming Habit: This plant blooms profusely and continuously.
Size of Bloom: Medium, averaging 5.1 cm. in diameter and 2 cm. in depth.
Borne: Singly on individual stems which branch in spray arrangement from a sturdy cane.
Shape: Flat and shape does not change as blo.ssom matures.
Petalage: Number of petals—averaging 32.
*Form.*—Fan shaped and serrated.
*Arrangement.*—Somewhat imbricated.
*Color.*—Outer petal—Red - Purple Group 61A. Base—Same as outer petal but less brilliant. Inside Petal—Red-Purple Group 61A. Reverse side—Red-Purple Group 71B.
*Appearance.*—Satiny.
*Texture.*—Soft.
Petaloids: About 8 in number.
*Size.*—About one-half of that of normal petals.
Peduncle: Medium length, upright and Greyed-Green in color.
Persistence: Petals hang on and dry.
Fragrance: Perceptible.
Effect of Weather: Blooms are not affected by wet or hot weather.
Lasting Quality:
*On Plant.*—13 days.
*As Cut Flower.*—7 to 10 days.
Disease Resistance: The plant has good resistance to the ordinary carnation diseases and particularly *Fusarium Roseium* and rust.

REPRODUCTIVE ORGANS

Stamens:
*Anthers.*—Average about 10 in number, 3 mm. long and of random arrangement.
*Filaments.*—2.5 cm. long. Color—White with Lavender at top.
*Pollen.*—Yellowish in color.
Pistils: 3.5 cm. long when ripen.
*Stigmas.*—Light Violet in color.
Ovaries: Globulus.

FRUIT

Fertility: The fruit of this variety is fertile.
Shape: Oblong.
Color: Green and Ochreous at maturity.

This variety of carnation plant most nearly resembles the variety Royalette (unpatented) and is distinguished from Royalette by its much higher productivity. This plant is further distinguished by its inflorescence which provides a spray of violet blossoms each appearing on a relatively long, strong stem.

The claim:

1. The new and distinct variety of carnation plant substantially as herein shown and described, characterized by its improved habit of growth and productivity, the absence of splitting, and the uniform coloring of its blossoms.

No references cited.

ROBERT E. BAGWILL, Primary Examiner